(12) United States Patent
da Luz

(10) Patent No.: US 7,118,739 B2
(45) Date of Patent: Oct. 10, 2006

(54) **BIOCONTROL OF PLANT DISEASES CAUSED BY *FUSARIUM* SPECIES WITH NOVEL ISOLATES OF *PANTOEA AGGLOMERANS***

(75) Inventor: Wilmar Cório da Luz, Passo Fundo (BR)

(73) Assignee: Empresa Brasileria de Pesquisa Agropecuaria - Embrapa, (BR)

( * ) Notice: Subject to any disclaimer, the term of this patent is extended or adjusted under 35 U.S.C. 154(b) by 429 days.

(21) Appl. No.: 10/459,513

(22) Filed: Jun. 12, 2003

(65) Prior Publication Data

US 2003/0211081 A1 Nov. 13, 2003

Related U.S. Application Data

(62) Division of application No. 10/004,798, filed on Dec. 7, 2001, now Pat. No. 6,599,503.

(30) Foreign Application Priority Data

Dec. 8, 2000 (BR) .................................. 0009629

(51) Int. Cl.
*A01N 63/00* (2006.01)
*C12N 1/20* (2006.01)

(52) U.S. Cl. .................. 424/93.3; 424/93.4; 424/93.46; 424/252.1

(58) Field of Classification Search ............... 424/93.3, 424/93.4, 93.46; 435/252.1
See application file for complete search history.

(56) References Cited

U.S. PATENT DOCUMENTS

| | | | |
|---|---|---|---|
| 5,403,583 A | 4/1995 | Liu et al. | |
| 5,494,819 A | 2/1996 | Soma et al. | |
| 5,552,315 A * | 9/1996 | Slininger et al. | 435/253.3 |
| 5,766,926 A | 6/1998 | Blanchette et al. | |
| 5,919,446 A * | 7/1999 | Pusey | 424/93.4 |
| 6,471,741 B1 | 10/2002 | Reinbergen | |

FOREIGN PATENT DOCUMENTS

| | | |
|---|---|---|
| DE | 19652580 | 7/1998 |
| EP | 0 441 520 A1 | 8/1991 |
| EP | 0 257 756 B1 | 1/1994 |
| WO | WO 92/18613 | 10/1992 |
| WO | WO 99/05257 | 2/1999 |

OTHER PUBLICATIONS

Boehm, M.J., et al., "USDA-ARS, Ohio State University Cooperative Research on Biologically Controlling Fusarium Head Blight: 3. Field Testing of Antagonists", Proceedings of the 1999 National Fusarium Head Blight Forum, Michigan State University, pp. 45-48, Dec. 5-7, 1999.

Cook, C.G., et al., "1987 Proceedings—Beltwide Cotton Production Research Conferences", "Effect of Treatment with *Bacillus* Species on Cotton Root Traits, Yield, and Phymatotrichum Root Rot", National Cotton Council of America, pp. 43-45, Jan. 4-8, 1987.

Costa Neto, J.P, da, "Lista de Fungos Sobre Gramineas (Capins e Cereais) no Rio Grande do Sul", *Revista da Faculdade de Agronomia*, UFRGS 1:43-78, 1976.

Islam, K.Z., et al., "Inhibition of Some Fungal Pathogens of Host Phylloplane by *Bacillus megaterium*", *Journal of Plant Diseases and Protection* 92(3):233-240, 1985.

Islam, K.Z., et al., "Control of Brown Spot of Rice by *Bacillus megaterium*", *Journal of Plant Diseases and Protection* 92(3):241-246, 1985.

Kahn, N.I., et al., "Biological Control of Scab of Wheat Incited by *Giberella zeae*", Proceedings of the *1998 National Fusarium Head Blight Forum*, Michigan State University, pp. 45-46, 1998.

Kahn, N.I., et al., "USDA-ARS, Ohio State University Cooperative Research on Biologically Controlling Fusarium Head Blight: 2. Influence of Pathogen Strain, Inoculum Spray Sequence and Inoculum Spray Time", Proceedings of the 1999 National Fusarium Head Blight Forum, Michigan State University, pp. 56-59, 1999.

Kern, H., "Phytotoxins Produced by Fusaria", In *Phytotoxins in Plant Disease*, Wood, R.K.S. et al, ed., Academic Press, New York, Ch 3., 1972.

Luo, Y., et al., "Biological Control of Fusarium Head Blight (FHB) of Wheat by Bacillus strains", Proceedings of the 1999 National Fusarium Head Blight Forum, Michigan State University, p. 60 (Abstract), 1999.

Luz, W.C. da, "Biocontrol of Fusarium Head Blight in Brazil", *Proceedings of the 2000 National Fusarium Head Blight Forum*, Michigan State University, pp. 77-81, 2000.

(Continued)

*Primary Examiner*—Herbert J. Lilling
(74) *Attorney, Agent, or Firm*—Finnegan, Henderson, Farabow, Garrett & Dunner LLP

(57) ABSTRACT

Microbiological agents are provided for control of certain diseases of wheat and other cereals caused by *Fusarium* species, including *Fusarium* head blight of wheat and other cereals. These agents can also improve yield of wheat plants and cereals. The agents are novel isolates of *Pantoea agglomerans* and of *Bacillus megaterium* that exhibit the property of inhibiting fungal pathogens, particularly those produced by *Fusarium* species.

Biocontrol compositions, and methods of using them to control plant pathogen development on wheat and cereal plants and for increasing plant yield, are also provided. The biocontrol compositions comprise a mixture of at least one microorganism selected from the group consisting of *Pantoea agglomerans* and *Bacillus megaterium*.

7 Claims, No Drawings

OTHER PUBLICATIONS

Luz, W.C. da, "Microbiological Control of *Bipolaris sorokiniana* 'In Vitro'", *Fitopatol. Brasileira* 15(3):246-247 Sep. 1990.

Luz, W.C. da, "Biocontrol of Fungal Pathogens of Wheat with Bacteria and Yeasts", *5th Int'l. Congress of Plant Pathology*, Kyoto, Japan, Abstract #2-134, p. 348, 1988.

Luz, W.C. da, "Yield Losses Caused by Fungal Foliar Wheat Pathogens in Brazil", *Phytopathology* 74 (12):1403-1407, 1984.

Luz, W.C. da, "Diagnose das Doenças da Cevada No Brasil", Passo Fundo—EMBRAPA-CNPT, *Circular Técnica N'. 2*, pp. 5-24, 1982.

Perondi, N.L., et al., "Controle Microbiológical da Giberela do Trigo", *Fitopatol. Brasileira* 21(2):243-249, Jun. 1996.

Perondi, N.L., et al., "Antagonistas Potenciais de *Fusarium graminearum*", *Anais do 2° Simpósio de Controle Biológico*, Brasilia, DF, p. 128, 1990.

Perondi, N.L., et al., "Controle Microbiano da Giberela do Trigo em Campo", *Anais do II Simpósio de Controle Biológico*, Brasilia, DF. p. 129, 1990.

Picinini, E.C., et al., "Controle Químico da *Gibberella zeae* em Trigo Pelo Uso de Fungicidas Inibidores da Biossíntese do Ergosterol", *Fitopatol. Brasileira*. 19 (Supl.):273, 1994.

Schisler, D.A., et al., "USDA-ARS, Ohio State University Cooperative Research on Biologically Controlling Fusarium Head Blight: 1. Antagonist Selection and Testing on Durum Wheat", Proceedings of the 1999 National Fusarium Head Blight Forum, Michigan State University, pp. 78-81, Dec. 5-7, 1999.

Shaw, P.D., "Production and Isolation", in *Toxins in Plant Disease*, Durbin, R.D., ed. Academic Press, New York, Ch. 2, 1981.

Stackebrandt, E., et al., "Taxonomic Note: A Place for DNA-DNA Reassociation"; and 16S rRNA Sequence Analysis in the Present Species Definition in Bacteriology, *Int. J. Syst. Bacteriol.* 44(4):846-849, Oct. 1994.

Stockwell, C.A., et al., "Identification of Bioprotectants for Control of *Gibberella zeae*", Proceedings of the 2000 National Fusarium Head Blight Forum, Michigan State University, pp. 114-117, 2000.

Stockwell, C.A., et al., "Selection of Microbial Antagonists for Biological Control of Fusarium Head Blight of Wheats", Proceedings of the 1999 National Fusarium Head Blight Forum, Michigan State University, pp. 82-84, Dec. 5-7, 1999.

Stockwell, C.A., et al., "Biocontrol of Wheat Scab with Microbial Antagonists", *Phytopathology*, 82:S94, 1997 (Abstract).

Computer EPAB Abstract DE019652580 Arkadevitch et al., Jul. 1998.

Computer DWPI Abstract 1988-039667 Ikabe JP62298363 Jun. 1986.

* cited by examiner

BIOCONTROL OF PLANT DISEASES CAUSED BY *FUSARIUM* SPECIES WITH NOVEL ISOLATES OF *PANTOEA AGGLOMERANS*

This application is a divisional application of U.S. application Ser. No. 10/004,798, filed Dec. 7, 2001 now U.S. Pat. No. 6,599,503, the benefit of which is claimed, and the entire disclosure of which is hereby incorporated herein by reference.

FIELD OF THE INVENTION

The present invention is related to the biological control of plant diseases caused by *Fusarium* species. Specially, it relates to biocontrol compositions comprising a mixture of at least one microorganism which is an antagonist against plant pathogens and an appropriate carrier, as well as to a process for control of the plant pathogen and to increase yield. The invention includes as a plant pathogen the pathogenic fungus *Gibberella zeae* (anamorph *Fusarium graminearum*), and as antagonist microorganisms the novel isolates of *Pantoea agglomerans* (Embr. 1494, Accession ATCC PTA 3460) and of *Bacillus megaterium* (Embr. 9790, Accession ATCC PTA 3461).

BACKGROUND OF INVENTION

Fruit, vegetables, and plants are all susceptible to attack by fungi, resulting in loss of crops, decreased shelf-life of produce, and ultimately higher costs for consumers. Many fungi are known pathogens in several diseases which harm or destroy crops worldwide. Examples of such fungi include those belonging to the genera *Rhizoctonia, Pythium, Gaeumannomyces*, and *Fusarium*.

For a number of years, it has been known that various microorganisms exhibit biological activity useful in controlling plant diseases. Although progress has been made in the field of identifying and developing biological pesticides for controlling plant diseases of agronomic and horticultural importance, most of the pesticides in use are still synthetic compounds. Many of the chemical fungicides are carcinogenic agents and, therefore, toxic to wildlife and other non-target species. In addition, pathogens may develop resistance to chemical pesticides. In fact, the fungicides, considered the major weapon in combating plant diseases, are often ineffective and pose hazards to humans and the environment. Biological control offers an attractive approach as compared with synthetic chemical fungicides. Biopesticides (living organisms and the compounds which are naturally produced by these organisms) can be safer, more biodegradable, and less expensive to develop. In addition, they are highly desired for integrated pest management programs in agriculture, public health, and urban settings.

The agricultural use of *Bacillus megaterium* has been reported for disease control in rice and cotton inhibition as seed treatment but not as foliar sprays. U.S. Pat. No. 5,403,583 discloses a *Bacillus megaterium*, ATCC 55000, and a method to control the fungal plant pathogen *Rhizoctonia solani* as seed treatment. Islam and Nandi also disclosed a *Bacillus megaterium* with antagonism to *Drechslera oryzae*, the causal agent of rice brown spot (Journal of Plant Diseases and Protection. 92(3): 241–246 (1985) and a *Bacillus megaterium* with in vitro antagonism against *Drechslera oryzae, Alternaria alternata* and *Fusariun roseum* (Journal of Plant Diseases and Protection. 92(3): 233–240 (1985). They mentioned three components in the culture filtrate. The most active antibiotic was highly soluble in water and methanol with a UV peak at 255 nm and a shoulder at 260 nm, which proved to be a polyoxin-like lipopeptide. And, Cook (Proceedings Beltwide Cotton Production-Mechanization Research Conference, Cotton Council, Memphis, p. 43–45 (1987) disclosed the use of a suspension of *Bacillus megaterium* to reduce the number of plants killed by *Phymatotrichum omnivorum*, a cause of cotton root rot. Antibiotic production of *B. megaterium* has also been recorded by Berdy (CRC Handbook of Antibiotic Compounds, Vols. I–XIV. CRC Press, Inc. Boca Raton. Fla. 1980–87), who reported the production of low-mammalian toxic peptide antibiotics such as ansamitocin-PDM-O, bacimethrin, megacin, pentapeptide, and homopeptides.

U.S. Pat. No. 5,494,819 describes a pure culture of *Pantoea agglomerans* having all of the characteristics of FERM BP-3511 which is identified by growth, morphology, physiology, utilization of carbon sources and various specific enzymatic tests involving enzymes as lysine decarboxylase, arginine dihydroxylase, phenylalanine deaminase and ornithine decarboxylase. In addition, the disclosed pure culture of *Pantoea agglomerans* is characterized by the required production of lipopolysaccharides to which the inventors attribute an immunity-stimulating activity. In other words, according to this document, *Pantoea agglomerans* is used to obtain substances to be used in pharmaceuticals.

U.S. Pat. No. 5,766,926 discloses a method comprising the steps of applying to the pulpwood or pulp substrate a bacterial inoculum of at least one of the species selected from the group consisting of *Pseudomonas fluorescens, Pantoea (Enterobacter) agglomerans, Bacillus cereus*, and *Xanthomonas campestris* and maintaining the substrate under conditions which allow bacterial growth for a time sufficient to effect a reduction in the resin component of the substrate by the bacteria. It is mentioned that the source of the *Pantoea (Enterobacter) agglomerans* isolate used in the method, identified by the NRRL Accession No.B21509, is Brazil.

It is known that the genus *Fusarium* contains species which may cause diseases of wither and blight that occur during the growth of plants and damages not only the host but also other kinds of plants. It is supposed that fusaric acid is the principal agent that brings about these diseases. Fusaric acid (5-n-butylpicolinic acid) is known to be a non-specific toxin which is produced by the metabolism of almost all plant pathogenic *Fusarium* fungi (Wood, R. K. et al. 1972. "Phytotoxins in plant diseases". Academic Press. New York; Durbin, R. D. 1982. "Toxins in plant diseases". Academic Press. New York). In the document EP 257 756, referring to the prevention of *Fusarium* diseases and microorganisms therefor, the inventors proposed to prevent such diseases by using microorganisms belonging to the genera *Cladosporium* and *Pseudomonas* which decompose fusaric acid. EP 441 520 relates also to detoxifying fusaric acid microorganisms, and *Klebsiella oxytoca* HY-1 (FERM BP-3221) is particularly mentioned.

In the document WO 92018613, it is suggested to control plant diseases caused by fungi of the genera *Rhizoctonia, Pythium*, and *Fusarium* by using a new strain of *Pseudomonas fluorenscens*, a seed or soil treatment but not foliar sprays.

WO 9905257, referring to biocontrol for plants with *Paenibacillus macerans, Pseudomonas putida*, and *Sporobolomyces roseus*, describes the use of isolates of these microorganisms to impart pathogen protection to plants, particularly against plant diseases caused by fungi, such as

*Fusarium oxysporum, Fusarium graminearum, Fusarium monilforme, Cochliobolus sativus, Collectotrichum graminicola, Stagonospora nodorum, Stagonospora avenae, Stenocarppela maydis*, and *Pyrenophora tritici-repentis*. In this case, pathogen protection was achieved by either seed treatment or foliar sprays.

*Fusarium graminearum* Schw. (Teleomorph=*Gibberella zeae* Schw. Petch.) is the *Fusarium* species most frequently responsible for scab of wheat and barley in Brazil. This disease, also known as *Fusarium* Head Blight (FHB), is responsible for major losses which vary from 10% (see Luz, W. C. da. 1984. "Yield losses caused by fungal foliar wheat pathogens in Brazil". *Phytopathology.* 74:1403–1407); to 54% (Picinini, E. C. and Fernandes, J. M. C. 1994. "Controle quimico da *Gibberella zeae* em trigo pelo uso de fungicidas inibidores da síntese do ergoterol". *Fitopatol. Brasileira* 19 (Supl.):273). At present, available and affordable control measures, such as resistant varieties, cultural practices, and foliar fungicides, are only partially effective.

Only modest levels of resistance have been deployed in cultivars in commercial fields; the most widely grown cultivars are often most susceptible. Furthermore, the benefit of crop rotation as a control measure is reduced by the wide host range of the pathogen, especially on grasses (Costa Neto, J. P. da. 1976. "Lista de fungos sobre gramíneas (capins e cereais) no Rio Grande do Sul". *Revista da Faculdade de Agronomia*. UFRGS. 1:43–78; Luz, W. C. da. 1982. "Diagnose das Doencas da Cevada". Passo Fundo—EMBRAPA-CNPT, 24p. (Circular Técnica no. 2)). Treatment with foliar fungicides remains the most important (Picinini and Fernandes, 1994) and recommended (Reunião da Comissão Sul-Brasileira de Pesquisa de Trigo, 2000) tool for reducing scab in Brazil, despite its shortcomings as a control measure. The use of certain effective fungicides has been restricted in some countries because application at late developmental stages, that is, during heading and flowering, can result in chemical residues in the harvested grain. Biological control is an additional strategy that may eventually play an important role in an integrative approach to scab management of cereals.

Screening of microorganisms to control wheat scab was initiated in Brazil in the 1980's (Luz, W. C. da. 1988. "Biocontrol of fungal pathogens of wheat with bacteria and yeasts". Page 348 in: 5$^{th}$ International Congesss of Plant Pathology, Kyoto, Japan. (Abstr.)). At the beginning, over 300 bacteria and yeasts isolated from wheat were screened in vitro against *F. graminearum*. This work was followed by that of Perondi et al. (Perondi, N. L., Thomas, R. and Luz, W. C. da. 1990. "Antagonistas potenciais de *Fusarium graminearum*". In: *Anais do 2° Simpósio de Controle Biológico*, Brasilia, D. F., p. 128. (Abstr.); Perondi, N. L., Thomas, R. and Luz, W. C. da. 1990. "Controle microbiano da giberela do trigo em campo". In: *Anais do II Simpósio de Controle Biológico*, Brasilia, D F. P.129(Abstr.); Perondi, N. L., Luz, W. C. da. and Thomas, R. 1996. "Controle microbiológico da giberela do trigo". *Fitopatol. Brasileira* 21:243–249) in which microbial strains were tested for their antagonistic action against the pathogen. Potential antagonists were selected by the funnel method (Luz, W. C. da. 1990. "Microbiological control of *Bipolaris sorokiniana* 'in vitro'". *Fitopatol. Brasileira* 15:246–247) which compared the effect of individual test organisms on the radial growth of *F. graminearum*. Promising isolates were further tested in the greenhouse and in the field for their ability to control wheat scab. Individual bioprotectants significantly diminished the severity of the disease under field conditions, raising the yield of wheat between 7 and 31% when compared to non-treated plants.

Besides the selection of the bioprotectants, it is important to overcome several difficulties related to constraints on their application to the ears of wheat and barley at flowering such as the timing of application, inoculation technology, physiological state of the organisms, spike colonization, survival of the organisms under the harsh environmental conditions, variability of biocontrol from year to year, fermentation, formulation, and storage. The partial control of any tactics to protect against FHB up to this moment indicates that the integration of protection measures would provide the best disease management.

From 1988 up to now, thousands of microorganisms have been tested for scab control. Some workers have been investigating antagonists to control FHB (Khan, N. J., Schisler, D. A., Boehm, M. J., Lipps, P. E., Slininger, P. J. and Bothast, R. J. 1998. "Biological control of scab of wheat incited by *Giberella zeae*". Pages 45–46 in: *Proceedings of the* 1998 *National Fusarium Head Blight Forum*, Michigan State University, University Printing, East Lansing. Mich.; Khan, N. J., Schisler, D. A., and Boehm, M. J. 1999. USDA-ARS, Ohio State University cooperative research on biologically controlling *Fusarium* Head Blight: 2. Influence of pathogen strain, inoculum spray sequence and inoculum spray time. Pages 56–59 in: *Proceedings of the* 1999 *National Fusarium Head Blight Forum*, Michigan State University, University Printing, East Lansing, Mich.; Boehm, m. J., Khan, N. J., and Schisler, D. A. 1999. USDA-ARS, Ohio State University cooperative research on biologically controlling *Fusarium* Head Blight: 3. Field testing of antagonists. Pages 45–48 in: *Preceedings of the* 1999 *National Fusarium Head Blight Forum*, Michigan State University, University Printing, East Lansing, Mich.; Luo, Y. and Bleakley, B. 1999. "Biological control of *Fusarium* Head Blight (FHB) of wheat by *Bacillus* strains". Pages 78–81 in: *Proceedings of the* 1999 *National Fusarium Head Blight Forum*, Michigan State University, University Printing, East Lansing, Mich.; Schisler, D. A., Khan, N. J., and Boehm, M. J. 1999. USDA_ARS, Ohio State University cooperative research on biologically controlling *Fusarium* Head Blight: 1. Antagosist selection and testing on durum wheat. Pages 78–81 in: *Proceedings of the* 1999 *National Fusarium Hrad Blight Forum*, Michigan State University, University Printing, East Lansing, Mich.; Stockwell, C. A., Luz, W. C. da., and Bergstrom, G. C. 1997. "Biocontrol of wheat scab with microbial antagonists". *Phytopathology* 87:S94.(Abstr.); Stockwell, C. A., Bergstrom, G. C., and Luz, W. C. da.1999. "Selection of microbial antagonists for biological control of *Fusarium* Head blight of wheat". Pages 82–84. in: *Proceedings of the* 1999 *National Fusarium Head Blight Forum*, Michigan State University, University Printing, East Lansing, Mich.; Stockwell, C. A., Bergstrom, G. C., and Luz, W. C. da. 2000. "Identification of bioprotectants for biological control of *Gibberella zeae*" in:. Proceedings of FHB Forum), under greenhouse or field conditions. Some strains have reduced the FHB severity and significantly reduced vomitoxin contamination in grains (Stockwell et al., 1997, 2000). Table 1 illustrates the chronology of researches on the biocontrol of FHB.

TABLE 1

Chronology of works done on biocontrol of *Fusarium* Head Blight of wheat

| LITERATURE | BIOPROTECTANTS |
| --- | --- |
| Lus, W.C. da, 1988 | Bacteria, Yeast |
| Perondi; N.L., Luz, W.C. da & Thomas, R, 1990 a, 1990 b, 1996 | *Bacillus subtilis* *Bacillus* spp. *Pseudomonas fluorescens* *Sporobolomyces roseus* |
| Stockwell, C.A; Luz, W.C. da, and Bergstrom, G.C. 1997 | *Paenibacillus macerans* *Pseudomonas putida* *Sporobolomyces roseus* |
| Khan, N.I., Scisler, D.A.. Bochm, M.J, Lipps, P.E., Slininger, P.J. and Bothast, R.J., 1998 | *Bacillus* spp. |
| Boehm, M.J., Khan., N.J., and Schisler, D.A, 1999 | Yeast, *Bacillus* sp. |
| Khan, N.J., and Schisler, D.A., and Boehm, M.J., 1999 | Yeast, *Bacillus* sp. |
| Luo, Y. & Bleakely, B. 1999 | *Bacillus* spp. |
| Schisler, D.A., Khan, N.J. and Boehm, M.J. 1999 | *Bacillus* spp. |
| Stockwell, C.A., Bergbstrom, G.C. and Luz, W.C. da. 1999 | *Paenibacillus macerans* *Pseudomonas putida* *Sporobolomyces roseus* |
| Stockwell, C.A., Bergstrom, G.C. and Luz, W.C. da., 2000 | *Paenibacillus macerans* *Bacillus* spp. |

SUMMARY OF THE INVENTION

According to the present invention, microbiological agents are provided for control of certain diseases of wheat and other cereals caused by *Fusarium* species, including *Fusarium* Head Blight (FHB) of wheat and other cereals. Moreover, these agents can also improve yield of said wheat plants and cereals. Specifically, these agents are novel isolates of *Pantoea agglomerans* and of *Bacillus megaterium* that exhibit the property of inhibiting fungal pathogens, particularly those produced by *Fusarium* species.

The first embodiment of the invention refers to a biocontrol composition comprising a mixture of at least one microorganism which is antagonist against plant pathogens and a carrier for said at least one microorganism, wherein said at least one microorganism is a bacteria selected from the group consisting of *Pantoea agglomerans* and *Bacillus megaterium* and said at least one microorganism is present in an amount effective for inhibiting plant pathogen development.

A second embodiment is related to a process for controlling the plant pathogen development on wheat and cereal plants by applying a composition containing a carrier and at least one microorganism which is an antagonist against plant pathogens selected from the group of bacteria consisting of *Pantoea agglomerans* and *Bacillus megaterium* in an amount effective to inhibit plant pathogen development on said plant.

The third embodiment is related with a process for increasing plant yield characterized by a step of applying, particularly by spraying, to the plant a composition containing a carrier and at least one microorganism selected from the group of bacteria consisting of *Pantoea agglomerans* and *Bacillus megaterium* in an amount effective to increase yield of said plants or plants resulting from treated seeds.

DETAILED DESCRIPTION OF THE INVENTION

For purposes of clarity and a complete understanding of the invention, the following terms are defined.

"Plants" is used to mean the head part of the plant to be treated.

"*Pantoea agglomerans* (Embr. 1494)" means the bacterium isolate which was isolated by Embrapa and identified by the code "Embr. 1494".

"*Bacillus megaterium* (Embr. 9790)" means the bacterium isolate which was isolated by Embrapa and identified by the code "Embr. 9790".

"CFU" refers to the abbreviation of Colony Forming Unity which is frequently used to express the concentration of microorganisms present in a composition.

Microorganisms usable in the present invention were identified by the following procedure: (i) screening plants or agricultural commodities (e.g. the surface(s) of said plant or agricultural commodity) for the presence of useful microorganisms; (ii) recovering (e.g. by washing or rising from the plant or agricultural commodity) and isolating said microorganism(s); and (iii) testing said microorganism(s) for antagonistic activity against plant pathogens. However, it should be understood that said microorganism(s) may be obtained from sources other than said plants or agricultural commodities.

The isolates of the present invention, Accession No. ATCC PTA 3460 (Embr. 1494) deposited at the ATCC (Manassas, Va.) on May 29, 2001, and Accession No. ATCC PTA 3461 (Embr. 9790) deposited at the ATCC (Manassas, Va.) on May 29, 2001, were obtained from wheat or corn plant parts, such as healthy leaves, seeds or roots by repeatedly washing the plant parts with water. The organisms were thereafter plated and grown on any nutritionally rich medium sufficient to support growth of the organisms. Preferably, the medium is nutrient agar. ATCC PTA 3460 was identified as a novel isolate of *Pantoea agglomerans* (Embr. 1494) and ATCC PTA 3461 was identified as a novel isolate of *Bacillus megaterium* (Embr. 9790).

Isolate ATCC PTA 3461 (Embr. 9790) of *B. megaterium* has the following characteristics: it is a Gram-positive rod, spore-forming bacteria, and the bacterial identification was accomplished based on 16S rRNA gene sequence similarity (made by Microbe Inotech Laboratories, Inc on Apr. 21, 2000 by using PE Applied Biosystem's MicroSeq™ microbial identification software and database) demonstrating that the isolate is novel and belongs to the species *Bacillus megaterium* (details about this characterization method may be found in Stackebrandt, E. and Goebel, B. M. 1994. "Taxonomic Note: A Place for DNA—DNA Reassociation"; and 16S rRNA Sequence Analysis in the Present Species Definition in Bacteriology. *Int. J. Syst. Bacteriol.* 44:846–849).

Isolate ATCC PTA 3460 (Embr. 1494) of *P. agglomerans* has the following characteristics: it is a Gram-negative bacteria; and, based on fat acid analysis (CG FAME method), has a similarity coefficient of 0.648 and distance coefficient of 3.310 (a good match is one with a similarity coefficient greater than 0.5 and a distance coefficient of less than 7) made by the same laboratory.

Growth of isolates ATCC PTA 3460 (Embr. 1494) and ATCC PTA 3461 (Embr. 9790) may be effected under aerobic condition at any temperature satisfactory for growth of the microorganisms, i.e., from about 10° C. to about 30° C. The preferred temperature range is 20° C. to 25° C. The pH of the nutrient medium is about neutral, i.e., 6.6 to 7.3.

The incubation time is that time necessary for the isolates to reach a stationary phase of growth, preferably between 40 and 60 hours. Growth of isolates ATCC PTA 3461 (Embr. 9790) (*B. megaterium*) and ATCC PTA 3460 (*P. agglomerans*) (Embr. 1494) is preferably achieved at a temperature range of 21° C. to 23° C., with an incubation time of 45 to 50 hours, such that the cells are in the logarithmic phase of growth.

Isolates ATCC PTA 3461 (Embr. 9790) (*B. megaterium*) and ATCC PTA 3460 (Embr. 1494) (*P. agglomerans*) may be grown in any conventional test tube or shake flask for small fermentation runs. For large scale operations, the culture may be carried out in a suitable fermentation tank, under appropriate conditions provided by agitating and aerating the inoculated liquid medium. Following incubation, the isolates are harvested by conventional sedimentary methods (e.g. centrifugation) or filtering. Cultures are stored on nutrient agar at 4° C., but also at much lower temperature such as −170° C.

The bacteria of the present invention are useful to control plant pathogens by using, for example, air spraying.

The microorganisms of the present invention may be applied to wheat plants or other cereals in combination with various liquid and/or solid carriers and additives, including combination with fungicides.

In the liquid form, e.g. solutions or suspensions, the microorganisms may be mixed or suspended in water or in aqueous solutions. Suitable liquid diluents or carriers include water, aqueous solutions, petroleum distillates, or other liquid carriers.

Solid compositions can be prepared by dispersing the antagonist microorganisms in and on an appropriately divided solid carrier, such as peat, wheat, bran, vermiculite, clay, talc, bentonite, diatomaceous earth, fuller's earth, pasteurized soil, and the like. When such formulations are used as wettable powders, biologically compatible dispersing agents such as non-ionic, anionic, amphoteric, or cationic dispersing and emulsifying agents can be used.

In a preferred embodiment, the compositions contemplated herein prevent attack by *Fusarium* diseases upon plants, particularly cereal plants, such as wheat, barley, and corn and, when used in sufficient amounts, to act as fungi antagonist. They have a high margin of safety because they do not burn or injury the plant.

The compositions of the invention are so chemically inert that they are compatible with substantially any other constituents of the spray schedule. They may also be used in combination with biologically compatible pesticidal active agents as for example, herbicides, nematocides, fungicides, insecticides, and the like. They can also be used in combination with plant growth affecting substances, such as fertilizers, plant growth regulators, and the like, provided that such compounds or substances are biologically compatible.

The active constituents are used in a concentration sufficient to inhibit plant pathogen development of the targeted plant pathogen when applied to the cereal plant. As will be apparent to a skilled in the art, effective concentrations may vary depending upon such factors as: (a) the type of the plant or agricultural commodity; (b) the physiological condition of the plant or agricultural commodity; (c) the concentration of pathogens affecting the plant or agricultural commodity; (d) the type of disease injury on the plant or agricultural commodity; (e) weather conditions (e.g. temperature, humidity); and (f) the stage of plant disease. According to the invention, typical concentrations are those higher than $1 \times 10^2$ CFU/ml of carrier. Preferred concentrations range from about $1 \times 10^4$ to about $1 \times 10^9$ CFU/ml, such as the concentrations ranging from $1 \times 10^6$ to $1 \times 10^8$ CFU/ml. More preferred concentrations are those of from about 37.5 to about 150 mg/g of dry bacterial mass per of carrier (dry formulation) or per ml of carrier (liquid composition).

The compositions of the invention may be applied to the wheat plant or other cereals using conventional methods such as dusting, injecting, rubbing, rolling, dipping, spraying, or brushing, or any other appropriate technique which does not injury the wheat plant or other cereals to be treated. Particularly preferred is the spray method.

The following specific examples are presented to more particularly illustrate the invention and should not be construed as a limitation thereon.

EXAMPLE 1

Effect of Bioprotectant Microorganisms of the Present Invention on Radial Growth of *Gibberella zeae* in Vitro.

In paired treatments, the radial growth (cm) of *Gibberella zeae*, in the presence of the isolate ATCC PTA 3461., corresponding to *Bacillus megaterium* (Embr. 9790) and the isolate ATCC PTA 3460, corresponding to *Pantoea agglomerans* (Embr. 1494), was reduced substantially.

The antagonist activity of the isolated microorganisms was determined by using the Antibiosis method as described in Luz (1990). Thousands of microorganisms were tested against *Gibberella zeae*. Each isolate was transferred onto Petri dishes containing nutrient agar in a circular pattern by means of a small sterile glass funnel. After 48 hours of incubation at 22° C. to 25° C., an agar disk containing a *G. zeae* colony was transferred into the center of the ring-shaped colony of the bioagent or, in the control treatment, onto an uninoculated media plate. The plates were incubated under fluorescent lights at 22° C. and under a photoperiod of 12 hours, in a completely randomized design. The radial growth of the pathogen was measured after three to five days, and the result was 2.5 to 3.0 cm. Further measurements were made to permit the assessment of the experiment. The data were calculated as % inhibition.

The data were subjected to analysis of variance and the means calculated by the Fisher test.

The pathogen growth reduction varied from 74% to 79% for *B. megaterium* and 25% to 38% for *P. agglomerans*. The results are shown in Table 2. In this table, the means within a column are significantly different (at p=0.05) from each other if they are followed by different letters, according to Fisher's least significant difference test.

TABLE 2

Effect of bioprotectants on radial growth of *Gibberella zeae*

| TREATMENTS | RADIAL GROWTH | | % REDUCTION | |
|---|---|---|---|---|
| | run 1 | run 2 | run 1 | run 2 |
| Nontreated | 2.00 c | 3.5 c | — | — |
| ATCC PTA 3461 (*Bacillus megaterium*-Embr. 9790) | 0.42 a | 0.9 a | 79 | 74 |
| ATCC PTA 3460 (*Pantoea agglomerans*-Embr. 1494) | 1.23 b | 2.6 b | 38 | 25 |

EXAMPLE 2

Biocontrol of Wheat Scab (*Fusarium* Head Blight) Under Growth Chamber Conditions.

Cultivar and growth conditions—A susceptible wheat variety to be infected by *Fusarium* was produced in EMBRAPA-Centro Nacional de Pesquisa de Trigo (CNPT), Brazil. This cultivar was planted under growth chamber providing adequate environmental conditions. Healthy-like plants (without disease symptoms) were grown and transferred to suitable pots and maintained in 12 hours-period dark at 20° C.

Pathogen preservation and inoculum production—A pure culture of *G. zeae* isolate, obtained by EMBRAPA-Centro Nacional de Pesquisa de Trigo (CNPT), Brazil, onto a BDA containing streptomycin medium was stored at 4° C. to avoid previous bacteria growth. *F. graminearum* inoculum was obtained from conidia which have been inoculated onto a BDA medium. Sporogenesis was observed after 3–5 days from the inoculation.

Antagonists treatment—The isolates were assessed under growth chamber conditions at the stage of initial flowering. Ears were uniformly sprayed with a suspension containing each isolate. The ears were treated with suspensions containing only one isolate and in a concentration of approximately $10^7$ CFU/ml. There were nine replicates per treatment and one blank (water without microorganisms).

Pathogen Inoculation and disease assessment—The pathogen was inoculated 24 hours after antagonists treatment by spraying the ears with an aqueous suspension containing $10^4$ conidia of *G. zeae*/ml. The inoculated plants were stored in a humid chamber for 48 hours. The disease assessment was made 15 days after pathogen inoculation. Disease severity was assessed by calculating the percentage of the scabby spikelets.

Biocontrol agents namely, Isolate ATCC PTA 3461 (*Bacillus megaterium* (Embr. 9790)) and Isolate ATCC PTA 3460 (*Pantoea agglomerans* (Embr. 1494)) significantly reduced the percentage of scabby spikelets when tested in growth chambers either using fresh bacterial cells or fermented and dry preparations. The results are shown in Table 3. In this table, the means within a column are significantly different (at p=0.05) from each other if they are followed by different letters.

TABLE 3

Biocontrol of wheat scab (*Fusarium* head blight) as measured by decrease in disease severity under growth chamber conditions.

| TREATMENTS | DISEASE SEVERITY (%) | | | |
|---|---|---|---|---|
| | run 1 | run 2 | run 3 | run 4 |
| Nontreated | 54 b | 86 b | 62 c | 68 b |
| ATCC PTA 3461 (*Bacillus megaterium* (Embr. 9790) (fresh cell)) | 18 a | 12 a | 15 a | 14 a |
| ATCC PTA 3460 (*Pantoea agglomerans* (Embr. 1494) (fresh cell) | 21 a | 10 a | 12 a | 12 a |
| ATCC PTA 3461 (*Bacillus megaterium* (Embr. 9790)) (wettable powder) | — | — | 20 b | 24 b |
| ATCC PTA 3460 (*Pantoea agglomerans* (Embr. 1494)) (wettable powder) | — | — | 22 b | 18 b |

EXAMPLE 3

Biocontrol of Scab of Wheat Under Field Conditions.

Field experiment, plant treatment with the antagonists of the invention—The experiment was carried out in an agricultural Brazilian area which is used for scab of wheat microbiological control, where natural disease infection occurs. The wheat variety used in the test was a *Fusarium graminearum* susceptible variety. Wheat plants with each treatment (concentration of $10^7$ CFU) were sown in plots of 12 rows, 3 m long. The space between rows was 20 cm. Treated plots in each experiment were arranged in a randomized block design.

Wettable powder compositions containing, individually, isolate ATCC PTA 3461 (*B. megaterium*) and isolate ATCC PTA 3460 (*Pantoea aglomerans*) of the present invention were also assessed.

Disease Severity and Yield Assessment—After 15 days from the application of the antagonists of the invention to wheat plants, the natural disease severity was assessed. Yield was also calculated in kg/ha.

As shown in Table 4, Isolate ATCC PTA 3461 (*Bacillus megaterium* (Embr. 9790)) and Isolate ATCC PTA 3460 (*Pantoea agglomerans* (Embr. 1494)) significantly diminished the disease incidence up to 50% and severity up to 67% in the field and the yield increase varied from 809 to 861 kg/ha (Table 4).

These results show that the biological control measure using these two bioagents play an important role in the management of scab on wheat.

TABLE 4

Biocontrol of wheat scab (*Fusarium* Head Blight) as measured by decrease in incidence and severity of the disease, and yield impact under field conditions

| TREATMENTS | DISEASE | | YIELD |
|---|---|---|---|
| | Incidence | Severity | (kg/ha) |
| Nontreated | 60 b | 30 b | 3328 b |
| ATCC PTA 3461 (*Bacillus megaterium*-Embr. 9790) | 30 a | 10 a | 4189 a |
| ATCC PTA 3460 (*Pantoea agglomerans* Embr. 1494) | 29 a | 11 a | 4137 a |

The invention claimed is:

1. A biocontrol composition comprising a mixture of a) at least one microorganism which is an antagonist against plant pathogens and b) a carrier for said at least one microorganism, wherein said at least one microorganism is *Pantoea agglomerans* ATCC PTA 3460, and wherein said microorganism is present in an amount effective for inhibiting plant pathogen development.

2. The biocontrol composition according to claim 1, wherein the carrier is selected from the group consisting of water, aqueous solutions, slurries, solids, and dry powders.

3. The biocontrol composition according to claim 2, wherein the solid carrier is selected from the group consisting of peat, wheat, bran, vermiculite, clay, talc, bentonite, diatomaceous earth, fuller's earth, and pasteurized soil.

4. The biocontrol composition according to claim 2, wherein the dry powder carrier is a wettable powder.

5. The biocontrol composition according to claim 1, wherein said at least one microorganism is present in an amount ranging from about $1 \times 10^2$ to about $1 \times 10^9$ CFU/ml of carrier.

6. The biocontrol composition according to claim 1, wherein the plant pathogen belongs to the *Fusarium* species.

7. The biocontrol composition according to claim 1, wherein said composition further comprises an additive selected from the group consisting of fertilizers, pesticides, preservatives, su rfactants, wetting agents, buffering agents, coating agents, abrading agents, and mixtures thereof.

* * * * *

UNITED STATES PATENT AND TRADEMARK OFFICE
CERTIFICATE OF CORRECTION

| | | |
|---|---|---|
| PATENT NO. | : 7,118,739 B2 | Page 1 of 1 |
| APPLICATION NO. | : 10/459513 | |
| DATED | : October 10, 2006 | |
| INVENTOR(S) | : Wilmar Cório de Luz | |

It is certified that error appears in the above-identified patent and that said Letters Patent is hereby corrected as shown below:

On the title page, item (73), "Brasileria" should read --Brasileira--.

Column 10, line 64, "su rfactants," should read --surfactants,--.

Signed and Sealed this

Twenty-sixth Day of December, 2006

JON W. DUDAS
*Director of the United States Patent and Trademark Office*